US006245759B1

(12) United States Patent
Bilodeau et al.

(10) Patent No.: US 6,245,759 B1
(45) Date of Patent: Jun. 12, 2001

(54) TYROSINE KINASE INHIBITORS

(75) Inventors: Mark T. Bilodeau, Lansdale; Mark E. Fraley, North Wales; Randall W. Hungate, Lansdale, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/519,780

(22) Filed: Mar. 7, 2000

Related U.S. Application Data

(60) Provisional application No. 60/123,902, filed on Mar. 11, 1999.

(51) Int. Cl.[7] .................. C07D 487/04; C07D 413/14; A61K 31/535; A61K 31/519
(52) U.S. Cl. .................. 514/233.2; 544/281; 544/117; 514/258
(58) Field of Search .................. 544/281, 117; 514/258, 233.2

(56) References Cited

FOREIGN PATENT DOCUMENTS

WO 00/09495    2/2000  (WO) .

OTHER PUBLICATIONS

Burke, T. R., Jr., Stem Cells, vol. 12, pp. 1–6, 1994.
Amirkhosravi, A., et al., Platelets, vol. 10, pp. 285–292, 1999.
Eliceiri, B. P., et al., Molecular Cell, vol. 4, pp. 915–924, 1999.
Gerber, H–P, et al., Nature Medicine, vol. 5(6), pp. 623–628, 1999.
Brower, V., Nature Biotechnology, vol. 17, pp. 963–968, 1999.
Shibuya, M., et al., Oncogene, vol. 5 pp. 519–524, 1990.
Terman, B. I., et al., Oncogene, vol. 6, pp. 1677–1683, 1991.

*Primary Examiner*—John M. Ford
*Assistant Examiner*—Hong Liu
(74) *Attorney, Agent, or Firm*—J. Antonio Garcia-Rivas; Mark R. Daniel

(57) ABSTRACT

The present invention relates to pyrazolo-pyrimidinyl compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

3 Claims, No Drawings

TYROSINE KINASE INHIBITORS

RELATED APPLICATIONS

This application claims the benefit under 35 U.S.C. § 119(e) of U.S. Provisional Application 60/123,902, filed Mar. 11, 1999.

BACKGROUND OF THE INVENTION

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

Tyrosine kinases are a class of enzymes that catalyze the transfer of the terminal phosphate of adenosine triphosphate to tyrosine residues in protein substrates. Tyrosine kinases are believed, by way of substrate phosphorylation, to play critical roles in signal transduction for a number of cell functions. Though the exact mechanisms of signal transduction is still unclear, tyrosine kinases have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

The receptor-type tyrosine kinases are comprised of a large number of transmembrane receptors with diverse biological activity. In fact, about twenty different subfamilies of receptor-type tyrosine kinases have been identified. One tyrosine kinase subfamily, designated the HER subfamily, is comprised of EGFR, HER2, HER3, and HER4. Ligands of this subfamily of receptors include epithileal growth factor, TGF-α, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-U and P receptors, CSFIR, c-kit and FLK-II. Then there is the FLK family which is comprised of the kinase insert domain receptor (KDR). fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., $DN\&P$ 7(6):334–339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen $Oncogene$, 8:2025–2031 (1993), which is hereby incorporated by reference.

Both receptor-type and non-receptor type tyrosine kinases are implicated in cellular signaling pathways leading to numerous pathogenic conditions, including cancer, psoriasis and hyperimmune responses.

Several receptor-type tyrosine kinases, and the growth factors that bind thereto, have been suggested to play a role in angiogenesis, although some may promote angiogenesis indirectly (Mustonen and Alitalo, $J. Cell Biol.$ 129:895–898, 1995). One such receptor-type tyrsoine kinase is fetal liver kinase 1 or FLK-1. The human analog of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., $Oncogene$ 8(1):11–15, 1993). VEGF and KDR are a ligand-receptor pair that play an important role in the proliferation of vascular endothelial cells, and the formation and sprouting of blood vessels, termed vasculogenesis and angiogenesis, respectively.

Angiogenesis is characterized by excessive activity of vascular endothelial growth factor (VEGF). VEGF is actually comprised of a family of ligands (Klagsburn and D'Amore, $Cytokine \& Growth Factor Reviews$ 7:259–270, 1996). VEGF binds the high affinity membrane-spanning tyrosine kinase receptor KDR and the related fms-like tyrosine kinase-1, also known as Fit-1 or vascular endothelial cell growth factor receptor 1 (VEGFR-1). Cell culture and gene knockout experiments indicate that each receptor contributes to different aspects of angiogenesis. KDR mediates the mitogenic function of VEGF whereas Fit-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841–844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., *N. Engl. J. Med.*, 324, pp. 1–8, 1991).

Accordingly, the identification of small compounds which specifically inhibit, regulate and/or modulate the signal transduction of tyrosine kinases is desirable and is an object of this invention.

SUMMARY OF THE INVENTION

The present invention relates to compounds that are capable of inhibiting, modulating and/or regulating signal transduction of both receptor-type and non-receptor type tyrosine kinases. One embodiment of the present invention is illustrated by a compound of Formula I, and the pharmaceutically acceptable salts and stereoisomers thereof:

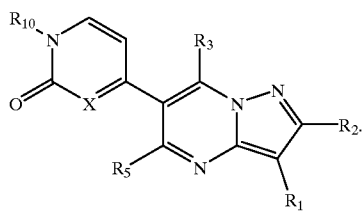

I

DETAILED DESCRIPTION OF THE INVENTION

The compounds of this invention are useful in the inhibition of kinases and are illustrated by a compound of Formula I:

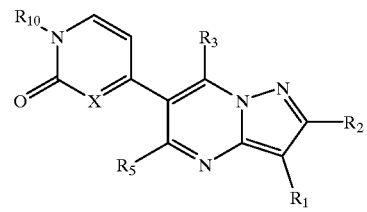

I or a pharmaceutically acceptable salt or stereoisomer thereof, wherein:

X is CH or N;

$R_1$ and $R_3$ are independently selected from the group consisting of:
1) W,
2) $C_{1-10}$ alkyl,
3) $C_{2-10}$ alkenyl,
4) $C_{2-10}$ alkynyl,
5) aryl,
6) halo,
7) OH, and
8) heterocyclyl,
said alkyl, alkenyl, alkynyl, aryl, and heterocyclyl is optionally substituted with one to three members selected from $R^a$;

$R_2$ is:
1) H,
2) $C_{1-6}$ alkyl,
3) aryl,
4) OH,
5) $NO_2$,
6) $NH_2$, or
7) halogen;

$R_5$ is:
1) H,
2) $C_{1-6}$ alkyl,
3) OH,
4) O—$C_{1-6}$ alkyl,
5) halo,
6) $NH_2$, or
7) $NO_2$;

$R_7$ and $R_8$ are independently selected from the group consisting of:
1) H,
2) $C_{1-10}$ alkyl,
3) COR,
4) COOR,
5) aryl, and
6) heterocyclyl,
said alkyl, aryl and heterocyclyl optionally substituted with $R_9$, or $NR_7R_8$ are be taken together to form a heterocyclic 5–10 membered saturated or unsaturated ring containing, in addition to the nitrogen atom, one to two additional heteroatoms selected from the group consisting of N, O and S, said ring optionally substituted with one or two substituents selected from $R^a$;

$R_9$ is aryl or heterocyclyl,
said aryl and heterocyclyl is optionally substituted with from one to three members selected from $R^a$;

$R_{10}$ is:
1) H,
2) $C_{1-6}$ alkyl,
3) $NR_7R_8$,
4) O—$C_{1-6}$ alkyl,
5) aryl, or
6) heterocyclyl,
said alkyl, aryl, and heterocyclyl is optionally substituted with one to three members selected from $R^a$;

$R^a$ is:
1) $C_{1-10}$ alkyl,
2) halogen,
3) $NO_2$,
4) OR,
5) $NR_7R_8$,
6) CN,
7) aryl, or
8) heterocyclyl; and R is H or $C_{1-6}$ alkyl.

A second embodiment is a compound of Formula 1, as described above, wherein $R_1$ and $R_3$ are independently selected from the group consisting of:
1) H,
2) $C_{1-10}$ alkyl,
3) aryl, and
4) heterocyclyl,
said alkyl, aryl, and heterocyclyl is optionally substituted with one to three members selected from $R^a$;

$R_2$ is:
1) H,
2) $C_{1-6}$ alkyl,
3) OH, or
4) halogen; and $R_{10}$ is:
1) $C_{1-6}$ alkyl,
2) $NR_7R_8$,
3) O—$C_{1-6}$ alkyl,
4) aryl,
5) heterocyclyl,
said aryl and heterocyclyl is optionally substituted with from one to three members selected from $R^a$.

And yet another embodiment is the compound of Formula I wherein X is CH. A further embodiment is a compound as described in the second embodiment above wherein X is further defined as CH.

And still another embodiment is a compound as described in the second embodiment above wherein X is further defined as CH and $R_1$ is selected from the group consisting of:
1) H,
2) $C_{1-10}$ alkyl,
3) phenyl, and
4) heterocyclyl,
aid alkyl, phenyl, and heterocyclyl is optionally substituted with one to three members selected from $R^a$;

$R_2$ is H or $C_{1-6}$ alkyl;
$R_3$ is H or $C_{1-3}$ alkyl;
$R_{10}$ is:
1) $C_{1-6}$ alkyl,
2) $NR_7R_8$,
3) O—$C_{1-6}$ alkyl,
4) phenyl,
5) heterocyclyl,
said phenyl and heterocyclyl is optionally substituted with from one to three members selected from $R^a$; and $R^a$ is:
1) $C_{1-6}$alkyl,
2) halogen,
3) $NO_2$,
4) OR,
5) $NR_7R_8$,
6) CN,
7) phenyl, or
8) heterocyclyl.

Yet another embodiment of the present invention is a compound which is 4-(3-phenyl-pyrazolo[1,5-a]pyrimidin-6-yl)-1-(3-piperidin-1-yl-propyl)-1H-pyridin-2-one:
1-(2-morpholin-4-yl-ethyl)-4-(3-phenyl-pyrazolo[1,5-a]pyrimidin-6-yl)-1H-pyridin-2-one;
1-(3-dimethylamino-propyl)-4-(3-phenyl-pyrazolo[1,5-a]pyrimidin-6-yl)-1H-pyridin-2-one;
1-(1-methyl-piperidin-3-ylmethyl)-4-(3-phenyl-pyrazolo[1,5-a]pyrimidin-6-yl)-1H-pyridin-2-one;
1-[3-(4-methylpiperazin-1-yl)-propyl)]-4-(3-phenyl-pyrazolo[1,5-a]pyrimidin-6-yl)-1H-pyridin-2-one;
1-(2-dimethylamino-propyl)-4-(3-phenyl-pyrazolo[1,5-a]pyrimidin-6-yl)-1H-pyridin-2-one;
1-(1-dimethylamino-2-methyl-propyl)-4-(3-phenyl-pyrazolo[1,5-a]pyrimidin-6-yl)-1H-pyridin-2-one;
1-[2-(4-cyano-piperidin-1-yl-ethyl]-4-(3-phenyl-pyrazolo[1,5-a]pyrimidin-6-yl)-1H-pyridin-2-one;
1-(3-piperidin-1-yl-propyl)-4-(3-thiophen-3-yl-pyrazolo[1,5-a]pyrimidin-6-yl)-1H-pyridin-2-one;
1-(3-piperidin-1-yl-ethyl)-4-(3-thiophen-3-yl-pyrazolo[1,5-a]pyrimidin-6-yl)-1H-pyridin-2-one;
1-(2-morpholin-4-yl-ethyl)-4-(3-thiophen-3-yl-pyrazolo[1,5-a]pyrimidin-6-yl)-1H-pyridin-2-one;
1-(3-dimethylamino-propyl)-4-(3-thiophen-3-yl-pyrazolo[1,5-a]pyrimidin-6-yl)-1H-pyridin-2-one;
1-(1-methyl-piperidin-3-ylmethyl)-4-(3-thiophen-3-yi-pyiazolo[1,5-a]pyrimidin-6-yl)-1H-pyridin-2-one;
1-[3-(4-methylpiperazin-1-yl)-propyl)]-4-(3-thiophen-3-yl-pyrazolo[1,5-a]pyrimidin-6-yl)-1H-pyridin-2-one;
1-(2-dimethylamino-propyl)-4-(3-thiophen-3-yl-pyrazolo[1,5-a]pyrimidin-6-yl)-1 H-pyridin-2-one;
1-(1-dimethylamino-2-methyl-propyl)-4-(3-thiophen-3-yl-pyrazolo[1,5-a]pyrimidin-6-yl)-1H-pyridin-2-one;
1-(3-di methylamino-propyl)-4-(3-thiophen-3-yl-pyrazolo[1,5-a]pyrimidin-6-yl)-1H-pyridin-2-one;
1-[2-(4-cyano-piperidin-1-yl-ethyl]-4-(3-thiophen-3-yl-pyrazolo[1,5-a]pyrimidin-6-yl)-1H-pyridin-2-one;
4-(3-phenyl-pyrazolo[1,5-a]pyrimidin-6-yl)-1-(3-piperidin-1-yl-propyl)-1H-pyrimidin-2-one;
1-(2-morpholin-4-yl-ethyl)-4-(3-phenyl-pyrazolo[1,5-a]pyrimidin-6-yl)-1H-pyrimidin-2-one;
1-(3-dimethylamino-propyl)-4-(3-phenyl-pyrazolo[1,5-a]pyrimidin-6-yl)-1H-pyrimidin-2-one;
1-(1-methyl-piperidin-3-ylmethyl)-4-(3-phenyl-pyrazolo[1,5-a]pyrimidin-6-yl)-1H-pyrimidin-2-one;
1-[3-(4-methylpiperazin-1-yl)-propyl)]-4-(3-phenyl-pyrazolo[1,5-a]pyrimidin-6-yl)-1H-pyrimidin-2-one;
1-(2-dimethylamino-propyl)-4-(3-phenyl-pyrazolo[1,5-a]pyrimidin-6-yl)-1H-pyrimidin-2-one;
1-(1-dimethylamino-2-methyl-propyl)-4-(3-phenyl-pyrazolo[1,5-a]pyrimidin-6-yl)-1H-pyrimidin-2-one; and 1-[2-(4-cyano-piperidin-1-yl-ethyl]-4-(3-phenyl-pyrazolo [1,5-a]pyrimidin-6-yl)-1H-pyrimidin-2-one;

or a pharmaceutically acceptable salt or stereoisomer thereof.

Also included within the scope of the present invention is a pharmaceutical composition which is comprised of a compound of Formula I as described above and a pharmaceutically acceptable carrier. The present invention also encompasses a method of treating or preventing cancer in a mammal in need of such treatment which is comprised of administering to said mammal a therapeutically effective amount of a compound of Formula 1. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, gioblastomas and breast carcinoma.

Also included is a method of treating or preventing a disease in which angiogenesis is implicated, which is comprised of administering to a mammal in need of such treatment a therapeutically effective amount of a compound of Formula 1. Such a disease in which angiogenesis is implicated is ocular diseases such as retinal vascularization, diabetic retinopathy, age-related macular degeneration, and the like.

Also included within the scope of the present invention is a method of treating or preventing inflammatory diseases which comprises administering to a mammal in need of such treatment a therapeutically effective amount of a compound of Formula 1. Examples of such inflammatory diseases are rheumatoid arthritis, psoriasis, contact dermatitis, delayed hypersensitivity reactions, and the like.

Also included is a method of treating or preventing a tyrosine kinase-dependent disease or condition in a mammal which comprises administering to a mammalian patient in need of such treatment a therapeutically effective amount of a compound of Formula I. The therapeutic amount varies according to the specific disease and is discernable to the skilled artisan without undue experimentation.

A method of treating or preventing retinal vascularization which is comprised of administering to a mammal in need of such treatment a therapeutically effective amount of compound of Formula 1 is also encompassed by the present invention. Methods of treating or preventing ocular diseases, such as diabetic retinopathy and age-related macular degeneration, are also part of the invention. Also included within the scope of the present invention is a method of treating or preventing inflammatory diseases, such as rheumatoid arthritis, psoriasis, contact dermatitis and delayed hypersensitivity reactions, as well as treatment or prevention of bone associated pathologies selected from osteosarcoma, osteoarthritis, and rickets.

The invention also contemplates the use of the instantly claimed compounds in combination with a second compound selected from the group consisting of:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

Preferred angiogenesis inhibitors are selected from the group consisting of a tyrosine kinase inhibitor, an inhibitor of epidermal-derived growth factor, an inhibitor of fibroblast-derived growth factor, an inhibitor of platelet derived growth factor, an MMP inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGF. Preferred estrogen receptor modulators are tamoxifen and raloxifene.

Also included in the scope of the claims is a method of treating cancer which comprises administering a therapeutically effective amount of a compound of Formula 1 in combination with radiation therapy and/or in combination with a compound selected from the group consisting of:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

And yet another embodiment of the invention is a method of treating cancer which comprises administering a therapeutically effective amount of a compound of Formula 1 in combination with paclitaxel or trastuzumab.

These and other aspects of the invention will be apparent from the teachings contained herein.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid arthritis, and the like).

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomer's and both tautomeric forms are intended to be encompassed by the scope of the invention, even though only one tautomeric structure is depicted. For example, any claim to compound A below is understood to include tautometic structure B, and vice versa, as well as mixtures thereof.

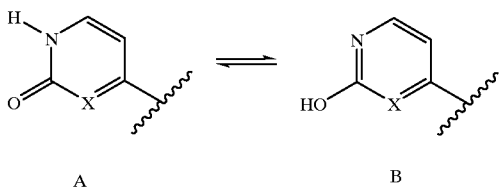

A        B

When any variable (e.g. aryl, heterocycle, $R^1$, $R^2$ etc.) occurs more than one time in any constituent, its definition on each occurrence is independent at every other occurrence. Also, combinations of substituents and variables are permissible only if such combinations result in stable compounds.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

As used herein, "alkyl" is intended to include both branched, straight-chain, and cyclic saturated aliphatic hydrocarbon groups having the specified number of carbon atoms. For example, $C_1$–$C_{10}$, as in "$C_1$–$C_{10}$ alkyl" is defined to include groups having 1, 2, 3, 4, 5, 6, 7, 8, 9 or 10 carbons in a linear. branched, or cyclic arrangement. For example, "$C_1$–$C_{10}$ alkyl" specifically includes methyl, ethyl, propyl, butyl, pentyl, hexyl, heptyl, octyl, nonyl, decyl, and so on, as well as cycloalkyls such as cyclopropyl, cyclobutyl, cyclopentyl, cyclohexyl, tetrahydronaphthalene, methylenecylohexyl, and so on. "Alkoxy" represents an alkyl group of indicated number of carbon atoms attached through an oxygen bridge.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$–$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$–$C_6$ alkynyl" means an alkynyl radical having from 2 to 6 carbon atoms. Alkynyl groups include ethynyl, propynyl and butynyl. As described above with respect to alkyl, the straight, branched or cyclic portion of the alkynyl group may contain triple bonds and may be substituted if a substituted alkynyl group is indicated.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. In cases where the heteroaryl substituent is bicyclic and one ring is non-aromatic or contains no heteroatoms, it is understood that attachment is via the aromatic ring or via the heteroatom containing ring, respectively.

As appreciated by those of skill in the art, "halo" or "halogen" as used herein is intended to include chloro, fluoro, bromo and iodo. The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

In certain instances, $R^7$ and $R^8$ are defined such that they can be taken together with the nitrogen to which they are attached to form a heterocyclic 5–10 membered saturated or unsaturated ring containing, in addition to the nitrogen atom, one to two additional heteroatoms selected from the group consisting of N, O and S, said ring optionally substituted with one or two substituents selected from $R^a$. Examples of the 5–7 membered ring systems that can thus be formed include, but are not limited to the following:

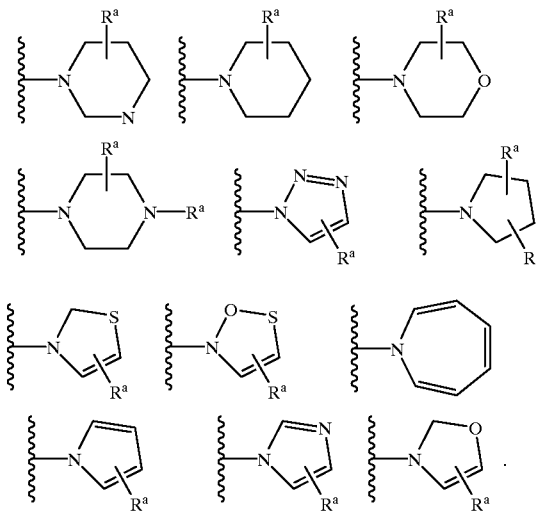

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The compounds of this invention may be prepared by employing reactions as shown in the following schemes, in addition to other standard manipulations that are known in the literature or exemplified in the experimental procedures. These schemes, therefore, are not limited by the compounds listed nor by any particular substituents employed for illustrative purposes. Substituent numbering as shown in the schemes do not necessarily con-elate to that used in the claims.

SCHEME 1

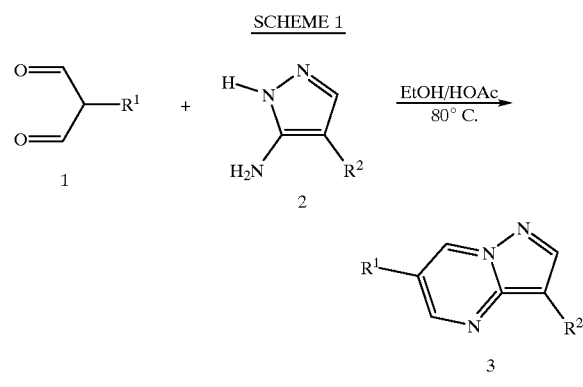

Generally, a method for the preparation of 3.6-diaryl pyrazolo(1,5-A)pyrimidines 3 comprises mixing a commercially available malondialdehyde compound 1 with a commercially available aminopyrazole 2 in an alcohol, such as ethanol, methanol, isopropanol, butanol and the like, said alcohol containing catalytic quantities of an acid, such as acetic acid.

SCHEME 2

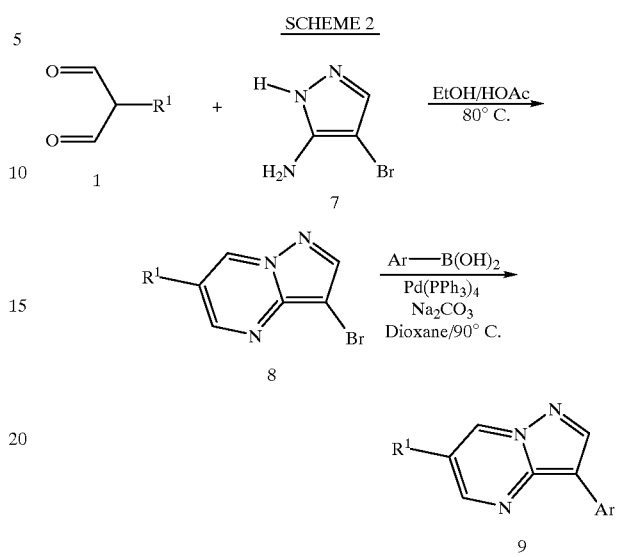

Scheme 2 illustrates one possible procedure for making 3,6-diaryl pyrazolo(1,5-A)pyrimidines 9 when the desired aminopyrazole is not commercially available. Compound 8 is obtained via the procedure described in Scheme I above. Subsequent treatment of 8 with a boronic acid derivative in the presence of a palladium catalyst provides the desired compound 9.

SCHEME 3

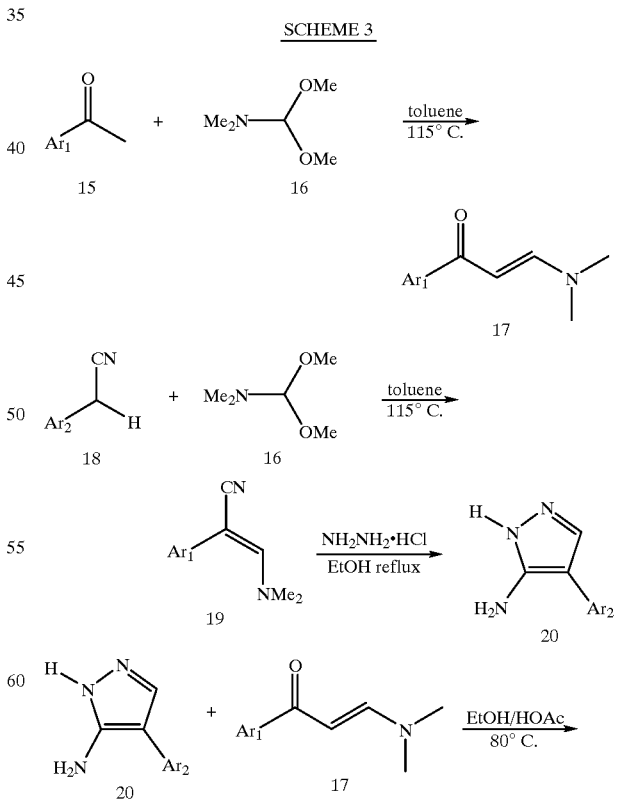

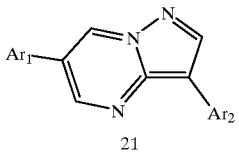

21

Scheme 3 illustrates an alternative method for the preparation of 3,7 diarylpyrazolo(1,5-A)pyrimidines 21. The commercially available ketone (15) and nitrite (18) are treated separately with dimethylformamidedi-methyl acetal (16) in refluxing toluene to give produce 17 and 19, respectively. Compound 19 is then treated with hydrazine-hydrochloride in refluxing ethanol to yield the aminopyrazole 20. Compounds 17 and 20 are then treated with catalytic amounts of acetic acid in ethanol as described previously giving the desired of 3,7 diarylpyrazolo(1,5-A) pyrimidines 21.

UTILITY

The instant compounds are useful as pharmaceutical agents for mammals, especially for humans, in the treatment of tyrosine kinase dependent diseases. Such diseases include the proliferation of tumor cells, the pathologic neovascularization (or angiogenesis) that supports solid tumor growth, ocular neovascularization (diabetic retinopathy, age-related macular degeneration, and the like) and inflammation (psoriasis, rheumatoid arthritis, and the like).

The compounds of the instant invention may be administered to patients for use in the treatment of cancer. The instant compounds inhibit tumor angiogenesis, thereby affecting the growth of tumors (J. Rak et al. *Cancer Research*, 55:4575–4580, 1995). The anti-angiogenesis properties of the instant compounds may also be useful in the treatment of certain forms of blindness related to retinal vascularization.

The disclosed compounds are also useful in the treatment of certain bone-related pathologies, such as osteosarcoma, osteoarthritis, and rickets, also known as oncogenic osteomalacia. (Hasegawa et al., Skeletal Radiol., 28, pp.41–45, 1999; Gerber et al., Nature Medicine, Vol. 5, No. 6, pp.623–628, June 1999).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, the instant compounds may be useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY 117081, toremifene, fulvestrant, 4-17-(2,2-dimethyl-1-oxopropoxy-4-methyl-2-[4-[2-(1-piperidinyl)ethoxylphenyl] -2H-1-benzopyran-3-yl]-phenyl-2,2-dimethylpropanoate, 4,4'-dihydroxybenzophenone-2,4-dinitrophenylhydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamideliarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, N-4-carboxyphenyl retinamide, "Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methylpyridine) platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN 10755, and 4-demethoxy-3-deamino-3-aziridinyl-4-methylsulphonyldaunorubicin.

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl )benzene sulfonamide, anhydrovinblastine, N,N-di methyl-L-valyl-L-valyl-N-methyl-L-valyl-L-prolyl-L-proline-t-butylamide, TDX258, and BMS 188797.

Some examples of topoisomerase inhibitors are topotecan, hycaptamine, irinotecan, rubitecan, 6-ethoxypropionyl-3',4'-O-exo-benzylidenechartreusin, 9-methoxy-N,N-dimethyl-5-nitropyrazolo[3,4,5-kl] acridine-2-(6H)propanamine, 1-amino-9-ethyl-5-fluoro-2,3-dihydro-9-hydroxy-4-methyl-1H,12H-benzo[de]pyrano[3', 4':b,7]indolizino[1,2b]quinoline-10,13(9H, 15H)dione, lurtotecan, 7-[2-(N-isopropylamino)ethyl]-(20S) camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa, 9b)-9-[2-[N-[2-(dimethylamino)ethyl ]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl) amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltit-exid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl ]-N'-(3,4-dichlorophenyl)urea, N6-[4-deoxy-4-[N2-[2(E),4(E)-tetradecadienoyl ]glycylamino] -L-glycero-B-L-manno-heptopyranosylladenine, aplidine, ecteinascidin, troxacitabine, 4-[2-amino-4-oxo -4,6,7,8-tetrahydro-31H-pynlrmidino[5,4-bl[1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911, 165; 4,929,437; 5,189,164; 5,118,853; 5,290,946; 5,356, 896), atorvastatin (LIPITOR®; see U.S. Pat. Nos. 5,273, 995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

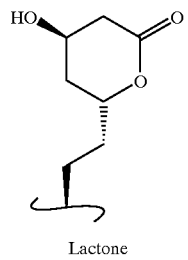

Lactone

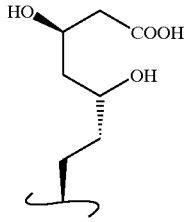

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, omithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate. polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2 (1H)-quinolinone, (−)-6-[amino(4-chlorophenyl)(1-methyl-1H-imidazol-5-yl)methyl]-4-(3-chlorophenyl)-1-methyl-2 (II)-quinolinone, (+)-6-[amino(4-chlorophenyl)(1-methyl-1H-imidazol-5-yl)methyl]-4-(3-chlorophenyl)-1-methyl-2 (1H1)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)—S—imidazolylmethyl]-5-[2-(ethanesulfonyl)methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl] piperidine, 4-{5-[4-Hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl) benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-Oxo- 2H-[1,2'] bipyridin-5'-ylmethyl]-3H-imidazol-4-ylmethyl}benzonitrile, 4-13-(2-Oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4]dioxaazacyclo-nonadecine-9-carbonitrile, (±)-19,20-Dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and (±)-19,20-Dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Pat. Publ. 0 618 221, European Pat. Publ. 0 675 112, European Pat. Publ. 0 604 181, European Pat. Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/2461 1, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp.1394–1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddl.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p.573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p.107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6—O—ch loroacetyl-carbonyl )-fumagillol, thalidomide, angiostatin, troponin-1, and antibodies to VEGF. (see, Nature Biotechnology, Vol. 17, pp.963–968 (October 1999); Kim et al., Nature, 362, 841–844 (1993)).

Other examples of angiogenesis inhibitors include, but arc not limited to, endostation, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1 H-1,2,3-triazole-4-carboxamide,CM101, squalamine, combretastatin, RP14610, NX31838, sulfated mannopentaose phosphate, 7,7-(carbonyl-bis[imino-N-methyl-4,2-pyrrolocarbonylimino[1-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_{v5}$, $\alpha_v\beta_6$, $\alpha_v\beta_8$, $\alpha_1\beta_1$, $\alpha_2\approx_1$, $\alpha_5\beta_1$, $\alpha_{6\beta 1}$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl) indolin-2-one, 17-(allylamino)-17-demethoxygeldanamycin, 4-(3-chloro-4-fluorophenylamino)-7-methoxy-6-[3-(4-morpholinyl) propoxyl]quinazoline, N-(3-ethynylphenyl)-6,7-bis(2-methoxyethoxy)-4-quinazolinamine, BIBX1382, 2,3,9,10, 11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD 121974.

The instant compounds are also useful, alone or in combination with platelet fibrinogen receptor (GP IIb/IIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, Platelets 10, 285–292, 1999). Therefore, the present compounds can serve to inhibit metastasis, alone or in combination with GP IIb/IIIa) antagonists. Examples of other fibrinogen receptor antagonists include abciximab, eptifibatide, sibrafiban, lamifiban, lotrafiban, cromofiban, and CT50352.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

Assays

The compounds of the instant invention described in the Examples were tested by the assays described below and were found to have kinase inhibitory activity. Other assays are known in the literature and could be readily performed by those of skill in the art. (see, for example, Dhanabal et al., Cancer Res. 59:189–197; Xin et al., J. Biol. Chew. 274:9116–9121; Sheu et al., Anticancer Res. 18:4435–4441; Ausprunk et al., Dev. Biol. 38:237–248; Gimbrone et al., J. Natl. Cancer Inst. 52:413–427; Nicosia et al., In Vitro 18:538–549).

VEGF Receptor Kinase Assay

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

Materials

VEGF Receptor Kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in *Spodoptera frugiperda* (Sf21) insect cells (Invitrogen) using a baculovirus expression vector (pAcG2T, Pharmingen).

Lysis Buffer 50 mM Tris pH 7.4, 0.5 M NaCl, 5 mM DTT, 1 mM EDTA, 0.5% triton X-100, 10% glycerol, 10 mg/mL of each leupeptin, pepstatin and aprotinin and 1 mM phenylmethylsulfonyl fluoride (all Sigma).
Wash Buffer
50 mM Tris pH 7.4, 0.5 M NaCl, 5 mM DTT, 1 mM EDTA, 0.05% triton X-100, 10% glycerol, 10 mg/mL of each leupeptin, pepstatin and aprotinin and 1 mM phenylmethylsulfonyl fluoride.
Dialysis Buffer
50 mM Tris pH 7.4, 0.5 M NaCl, 5 mM DTT, 1 mM EDTA, 0.05% triton X-100, 50% glycerol, 10 mg/mL of each leupeptin, pepstatin and aprotinin and 1 mM phenylmethylsuflonyl fluoride.
10× Reaction Buffer
200 mM Tris, pH 7.4, 1.0 M NaCl, 50 mM $MnCl_2$, 10 mM DTT and 5 mg/mL bovine serum albumin (Sigma).
Enzyme Dilution Buffer
50 mM Tris, pfl 7.4, 0.1 M NaCl, 1 mM DTT, 10% glycerol, 100 mg/mL BSA.
10× Substrate
750 μg/mL poly (glutamic acid, tyrosine; 4:1) (Sigma). Stop solution 30% trichloroacetic acid, 0.2 M sodium pyrophosphate (both Fisher).
Wash Solution
15% trichloroacetic acid, 0.2 M sodium pyrophosphate. Filter plates Millipore #MAFC NOB, GF/C glass fiber 96 well plate.
Method
A. Protein Purification
1. Sf21 cells were infected with recombinant virus at a multiplicity of infection of 5 virus particles/cell and grown at 27° C. for 48 hours.
2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.
B. VEGF Receptor Kinase Assay
1. Add 5 μl of inhibitor or control to the assay in 50% DMSO.
2. Add 35 μl of reaction mix containing 5 μl of 10× reaction buffer, 5 μl 25 mM ATP/10 μCi [$^{33}$P]ATP (Amersham), and 5 μl 10 X substrate.
3. Start the reaction by the addition of 10 μl of KDR (25 nM) in enzyme dilution buffer.
4. Mix and incubate at room temperature for 15 minutes.
5. Stop by the addition of 50 Al stop solution.
6. Incubate for 15 minutes at 4° C.
7. Transfer a 90 μl aliquot to filter plate.
8. Aspirate and wash 3 times with wash solution.
9. Add 30 μl of scintillation cocktail, seal plate and count in a Wallac Microbeta scintillation counter.
Human Umbilical Vein Endothelial Cell Mitogenesis Assay
Expression of VEGF receptors that mediate mitogenic responses to the growth factor is largely restricted to vascular endothelial cells. Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials
HUVECs
HUVECs frozen as primary culture isolates are obtained from Clonctics Corp. Cells are maintained in Endothelial Growth Medium (EGM; Clonetics) and are used for mitogenic assays at passages 3–7.
Culture Plates
NUNCLON 96-well polystyrene tissue culture plates (NUNC #167008).
Assay Medium
Dulbecco's modification of Eagle's medium containing 1 g/mL glucose (low-glucose DMEM; Mediatech) plus 10% (v/v) fetal bovine serum (Clonetics).
Test Compounds
Working stocks of test compounds are diluted serially in 100% dimethylsulfoxide (DMSO) to 400-fold greater than their desired final concentrations. Final dilutions to 1X concentration are made directly into Assay Medium immediately prior to addition to cells.
10× Growth Factors
Solutions of human $VEGF_{165}$ (500 ng/mL; R&D Systems) and bFGF (10 ng/mL; R&D Systems) are prepared in Assay Medium.
10× [$^3$H]Thymidine
[Methyl-$^3$H]Thymidine (20 Ci/mmol; Dupont-NEN) is diluted to 80 uCi/mL in low-glucose DMEM.
Cell Wash Medium
Hank's balanced salt solution (Mediatech) containing 1 mg/mL bovine serum albumin (Boehringer-Mannheim).
Cell Lysis Solution
1N NaOH, 2% (w/v) $Na2CO_3$.
Method
1. HUVEC monolayers maintained in EGM are harvested by trypsinization and plated at a density of 4000 cells per 100 μL Assay Medium per well in 96-well plates. Cells are growth-arrested for 24 hours at 37 C in a humidified atmosphere containing 5% $CO_2$.
2. Growth-arrest medium is replaced by 100 μL Assay Medium containing either vehicle (0.25% (v/v) DMSO) or the desired final concentration of test compound. All determinations are performed in triplicate.
Cells are then incubated at 37° C./5% $CO_2$ for 2 hours to allow test compounds to enter cells.
3. After the 2-hour pretreatment period, cells are stimulated by addition of 10 μL/well of either Assay Medium, 10× VEGF solution or 10× bFGF solution. Cells are then incubated at 37° C/5% $CO_2$.
4. After 24 hours in the presence of growth factors, 10× [$^3$H]Thymidine (10 μL/well) is added.
5. Three days after addition of [$^3$H]thymidine, medium is removed by aspiration, and cells are washed twice with Cell Wash Medium (400 μL/well followed by 200 μL/well). The washed, adherent cells are then solubilized by addition of Cell Lysis Solution (100 μL/well) and warming to 37° C. for 30 minutes. Cell lysates are transferred to 7-mL glass scintillation vials containing 150 μL of water. Scintillation cocktail (5 mL/vial) is added, and cell-associated radioactivity is determined by liquid scintillation spectroscopy.
Based upon the foregoing assays the compounds of formula I are inhibitors of VEGF and thus are useful for the inhibition of angiogenesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with IC50 values between 0.01–5.0 μM. These compounds also show selectivity over related tyrosine kinases (e.g., FGFR1 and the Src family; for relationship

EXAMPLES

Examples provided are intended to assist in a further understanding of the invention. Particular materials employed, species and conditions are intended to be further illustrative of the invention and not limiting of the reasonable scope thereof.

Example 1

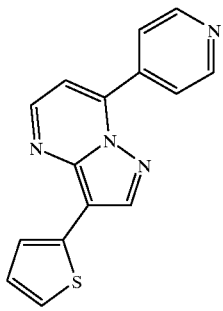

3-(3-thiophenyl)-7-(4-pyridyl)pyrazolo(1,5-A)pyrimidine

A 13×100 mm reaction tube was charged with aminopyrazole (22) (16.5 mg, 0.100 mmol) dissolved in 0.500 mL EtOH and vinylogous amide (23) (17.6 mg, 0.100 mmol) dissolved in 0.200 mL EtOH. Glacial acetic acid (1 drop) was added and the reaction was heated to 80° C. for 14 h. An additional 0.100 mL of glacial acetic acid was added and heating was continued for an additional 6 h. The sample was concentrated to dryness to provide the desired title compound. Analysis by mass spectrometry showed [M+H]+ 279.2.

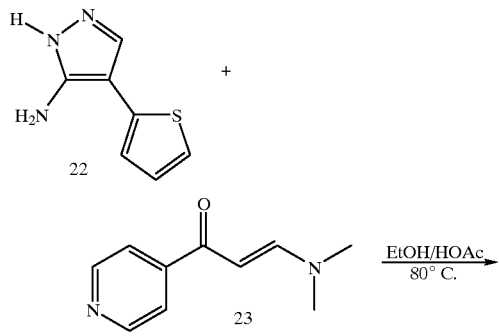

Example 2

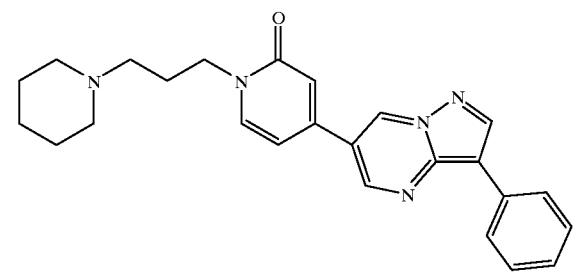

4-(3-phenyl-pyrazolo[1,5-a]pyrimidin-6-yl)-1-(3-piperidin-1-yl-propyl)-1H-pyridin-2-one Step 1:

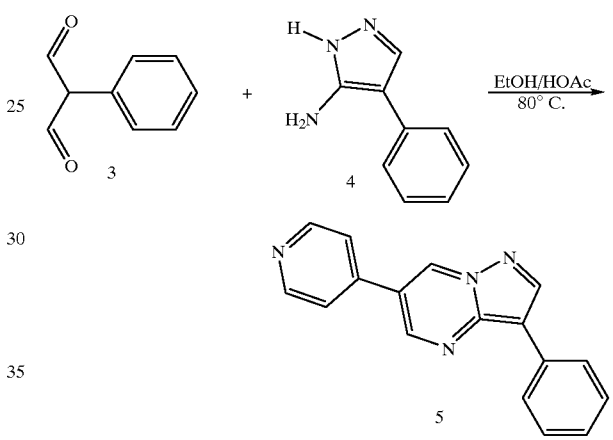

A solution of 2-(4-pyridyl)malondialdehyde (1.00 g, 6.70 mmol, 1 equiv) and 3-amino-4-phenylpyrazole (1.07 g, 6.72 mmol, 1.00 equiv) in absolute ethanol (50 mL) was heated at reflux for 2 h. The reaction mixture was allowed to cool to 23° C., and the resulting precipitate was filtered, washed with methanol (100 mL), and air dried to give 5 as a light yellow solid.

mp=226–228° C. $^1$H NMR (400 MHz, CDCl$_3$) δ 8.95 (d, 114, J=2.4 Hz), 8.85 (d, 1H, J=2.4 Hz), 8.78 (atypical dd, 2H, J=4.6, 1.6 Hz), 8.52 (s, 1H), 8.06 (dd, 2H, J=8.0, 1.1Hz), 7.55 (atypical dd, 2H, J=4.6, 1.6 Hz), 7.48 (t, 2H, J=7.9 Hz), 7.32 (td, 1H, J=8.2, 0.9 Hz); anal. calcd for C17H12N4: C, 74.98; H, 4.44; N, 20.58. Found C, 75.10; H, 4.56; N, 20.50.

Step 2:

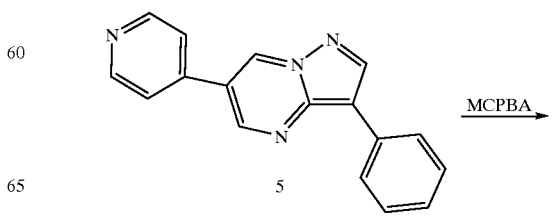

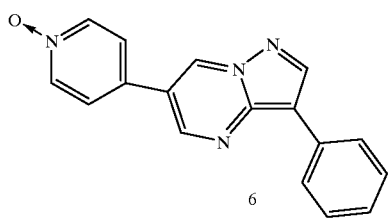

A solution of 5 (300 mg, 1. 10 mmol, 1 equiv) and 55% mCPBA (449 mg, 1.43 mmol, 1.30 equiv) in dichloromethane (50 mL) was stirred at 23° C. for 5 h. The precipitate was filtered, washed with dichloromethane (50 ml) and air dried to give 6 as a bright yellow solid.

¹H NMR (400 MHz, (CD₃)₂SO) δ 9.73 (d,1H, J=2.3 Hz), 9.14 (d, 1H, J=2.3 Hz), 8.86 (s, 1H), 8.37 (d, 2H, J=7.0 Hz), 8.18 (d, 2H, J=7.7 Hz),), 8.01 (d, 2H, J=7.3 Hz), 7.47 (t, 2H, J=8.0 Hz), 7.28 (t, 1H, J=7.4 Hz).

Step 3:

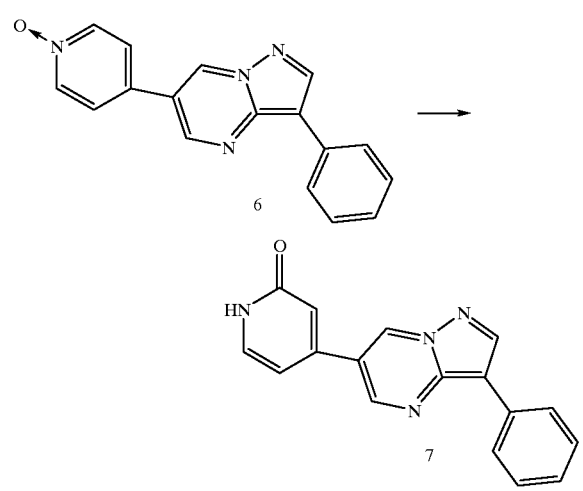

A solution of 6 (70 mg, 0.24 mmol, 1 equiv) in acetic anhydride (10 mL) was heated at reflux for 16 h. The reaction mixture was allowed to cool to 23° C., then concentrated. To a solution of the residue in anhydrous methanol (15 mL) was added potassium carbonate (50 mg, 0.36 mmol, 1.5 equiv), and the resulting mixture was stirred at 23° C. for 30 min. Excess potassium carbonate was removed by filtration, and the filtrate was concentrated. The residue was partitioned between water (100 ml) and ethyl acetate (2×50 ml). The combined organic layers were dried over sodium sulfate and concentrated to leave intermediate 7 as a brown solid.

¹H NMR (400 MHz, CDCl₃) δ 9.73 (d, 1H, J=2.3 Hz), 9.14 (d, 1H, J=2.3 Hz), 8.86 (s, 1H), 8.18 (d, 2H, J=7.7 Hz), ), 7.53 (d, 1H, J=6.7 Hz), 7.47 (t, 2H, J=7.8 Hz), 7.28 (t, 1H, J=7.6 Hz), 6.92 (d, 1H, J=1.2 Hz), 6.75 (dd, 1H, J=6.7, 1.2 Hz).

Step 4:

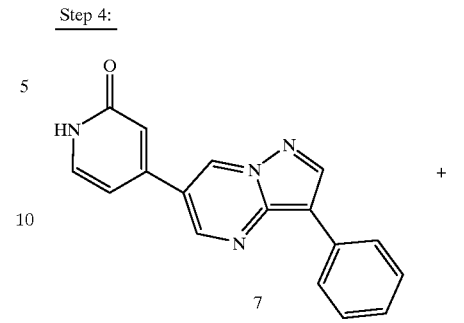

A mixture of unpurified 7 (50 mg, 0.17 mmol, 1 equiv), 1-(3-chloropropyl)piperidine hydrochloride (41 mg, 0.21 mmol, 1.2 equiv), cesium carbonate (136 mg, 0.416 mmol, 2.4 equiv), and sodium iodide (31 mg, 0.21 mmol, 1.2 equiv) in DMF (5 mL) was heated at 50° C. for 16 h. More 1-(3-chloropropyl)piperidine hydrochloride (34 mg, 0.17 mmol, 1.0 equiv), cesium carbonate (55 mg, 0.17 mmol, 1.0 equiv), and sodium iodide (25 mg, 0.17 mmol, 1.0 equiv) were added and the resulting mixture was heated at 60° C. for 7 h. At this point, additional 1-(3-chloropropyl) piperidine hydrochloride (34 mg, 0.17 mmol, 1.0 equiv), cesium carbonate (55 mg, 0.17 mmol, 1.0 equiv), and sodium iodide (25 mg, 0.17 mmol, 1.0 equiv) were added and heating (60° C.) was continued for 48 h. The reaction mixture was then partitioned between water (50 mL) and ethyl acetate (3×50 mL). The combined organic layers were dried over sodium sulfate and concentrated. The residue was purified by flash column chromatography (CHCl₃ sat'd with NH₃) to afford compound 8a as a yellow solid.

¹H NMR (400 MHz, CDCl₃) δ 8.88 (d, 1H, J=2.3 Hz), 8.79 (d, 1H, J=2.3 Hz), 8.51 (s, 1H), 8.05 (d, 2H, J=7.7 Hz), 7.56 (d, 1H, J=7.0 Hz), 7.48 (t, 2H, J=7.8 Hz), 7.31 (t, 1H, J=7.4 Hz), 6.84 (d, 1H, J=2.0 Hz), 6.39 (dd, 1H, J=7.0, 2.1 Hz), 4.07 (t, 2H, J=6.7 Hz), 2.36 (br m, 2H), 2.34 (t, 2H, J=6.9 Hz), 2.00 (pentet, 2H, J=6.8 Hz), 1.59 (brm, 6H), 1.45 (br m, 2H).

What is claimed is:
1. A compound in accordance with formula 1:

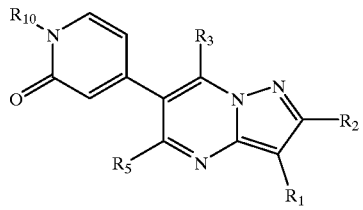

or a pharmaceutically acceptable salt or stereoisomer thereof, wherein
- $R_1$ is phenyl or thienyl, said phenyl and thienyl optionally substituted with one to three substituents selected from $R^a$;
- $R_2$, $R_3$, and $R_5$ are independently selected from H or C1–6 alkyl; $R_7$ and $R_8$ are independently selected from:
  2) $C_{1-6}$ alkyl,
  3) COR,
  4) COOR, and
  5) Phenyl; or
  $NR_7R_8$ can be taken together to form a heterocyclic 5–7 membered saturated or unsaturated ring consisting of, in addition to the nitrogen atom, one to two additional non-adjacent heteroatoms selected from N, O and S, said ring optionally substituted with one or two substituents selected from $R^a$;
- $R_{10}$ is:
  1) H,
  2) $C_{1-6}$ alkyl,
  3) $NR_7R_8$,
  4) O-$C_{1-6}$ alkyl
  5) phenyl,
  6) morpholinyl,
  7) piperizinyl, or
  6) piperidinyl;
  said alkyl, phenyl, morpholinyl, piperzinyl, and piperidinyl is optionally substituted with one to three members selected from Ra;
- $R^a$ is:
  1) $C_{1-10}$ alkyl,
  2) halogen,
  3) $NO_2$,
  4) OR,
  5) $NR_7R_8$,
  6) CN,
  7) phenyl,
  8) morpholinyl,
  9) piperizinyl, or
  10) piperidinyl;
  R is H or $C_{1-6}$ alkyl.

2. A compound selected from:
4-(3-phenyl-pyrazolo[1,5-a]pyrimidin-6-yl)-1-(3-piperidin-1-yl-propyl)-1H-pyridin-2-one;
1-(2-morpholin-4-yl-ethyl)-4-(3-phenyl-pyrazolo[1,5-a]pyrimidin-6-yl)-1H-pyridin-2-one;
1-(3-dimethylamino-propyl)-4-(3-phenyl-pyrazolo[1,5-a]pyrimidin-6-yl)-1H-pyridin-2-one;
1-(1-methyl-piperidin-3-ylmethyl)-4-(3-phenyl-pyrazolo[1,5-a]pyrimidin-6-yl)-1H-pyridin-2-one;
1-[3-(4-methylpiperazin-1-yl)-propyl]-4-(3-phenyl-pyrazolo[1,5-a]pyrimidin-6-yl)-1H-pyridin-2-one;
1-(2-dimethylamino-propyl)-4-(3-phenyl-pyrazolo[1,5-a]pyrimidin-6-yl)-1H-pyridin-2-one;
1-(1-dimethylamino-2-methyl-propyl)-4-(3-phenyl-pyrazolo[1,5-a]pyrimidin-6-yl)-1H-pyridin-2-one;
1-[2-(4-cyano-piperidin-1-yl)-ethyl]-4-(3-phenyl-pyrazolo[1,5-a]pyrimidin-6-yl)-1H-pyridin-2-one;
1-(3-piperidin-1-yl-propyl)-4-(3-thiophen-3-yl-pyrazolo[1,5-a]pyrimidin-6-yl)-1H-pyridin-2-one;
1-(3-pipeiidin-1-yl-ethyl)-4-(3-thiophen-3-yl-pyrazolo[1,5-a]pyrimidin-6-yl)-1H-pyridin-2-one;
1-(2-morpholin-4-yl-ethyl)-4-(3-thiophen-3-yl-pyrazolo[1,5-a]pyrimidin-6-yl)-1H-pyridin-2-one;
1-(3-dimethylamino-propyl)-4-(3-thiophen-3-yl-pyrazolo[1,5-a]pyrimidin-6-yl)-1H-pyridin-2-one;
1-methyl-piperidin-3-ylmethyl)-4-(3-thiophen-3-yl-pyrazolo[1,5-a]pyrimidin-6-yl)-1H-pyridin-2-one;
1-[3-(4-methylpiperazin-1-yl)-propyl]-4-(3-thiophen-3-yl-pyrazolo[1,5-a]pyrimidin-6-yl)-1H-pyridin-2-one;
1-(2-dimethylamino-propyl)-4-(3-thiophen-3-yl-pyrazolo[1,5-a]pyrimidin-6-yl)-1H-pyridin-2-one;
1-(1-dimethylamino-2-methyl-propyl)-4-(3-thiophen-3-yl-pyrazolo[1,5-a]pyrimidin-6-yl)-1H-pynidin-2-one;
1-(3-di methylamino-propyl)-4-(3-thiophen-3-yl-pyrazolo[1,5-a]pyrimidin-6-yl)-1H-pyridin-2-one;
1-[2-(4-cyano-piperidin-1-yl)-ethyl]-4-(3-thiophen-3-yl-pyrazolo[1,5-a]pyrimidin-6-yl)-1H-pyridin-2-one;
or a pharmaceutically acceptable salt or stereoisomer thereof.

3. A pharmaceutical composition which is comprised of a compound in accordance with claim 1 and a pharmaceutically acceptable carrier.

* * * * *

UNITED STATES PATENT AND TRADEMARK OFFICE
CERTIFICATE OF CORRECTION

PATENT NO. : 6,245,759 B1
DATED : June 12, 2001
INVENTOR(S) : Mark T. Bilodeau, Mark E. Fraley and Randall W. Hungate It is certified that error appears in the above-identified patent and that said Letters Patent is hereby corrected as shown below:

Column 27,
Line 20, after "C1-6" and before "2)", lines 21-23 should read as follows:

-- alkyl;
    $R_7$ and $R_8$ are independently selected from:
       1) H,
       2) $C_1$-$C_{10}$ alkyl, --.

Column 28,
Line 26, should read as follows:
-- 1-(3-piperidin-1-yl-ethyl)-4-(3-thiophen-3-yl-pyrazolo[1, --.
Line 33, should read as follows:
-- 1-(1-methyl-piperidin-3-ylmethyl)-4-(3-thiophen-3-yl- --.
Line 44, should read as follows:
-- 1-[2-(4-cyano-piperidin-1-yl)-ethyl]-4-(3-phenyl-3-yl- --.

Signed and Sealed this

Twelfth Day of November, 2002

Attest:

*Attesting Officer*

JAMES E. ROGAN
*Director of the United States Patent and Trademark Office*